United States Patent [19]
Dichter et al.

[11] 3,956,480
[45] May 11, 1976

[54] TREATMENT OF TEETH
[75] Inventors: Michael Dichter, Brooklyn; Durydehan Mangaraj, Staten Island, both of N.Y.; William James King, River Edge, N.J.
[73] Assignee: Colgate-Palmolive Company, New York, N.Y.
[22] Filed: July 1, 1974
[21] Appl. No.: 484,722

[52] U.S. Cl. .................................. 424/54; 424/49; 424/78; 424/79; 424/329
[51] Int. Cl.² .................. A61K 7/22; A61K 31/14; A61K 31/74
[58] Field of Search ............................. 424/49–58, 424/79, 329, 78, 48

[56] References Cited
UNITED STATES PATENTS
2,984,639 5/1961 Stamberger et al. ................ 424/329
3,397,990 8/1968 Hochstein .......................... 424/329

FOREIGN PATENTS OR APPLICATIONS
1,166,627 10/1969 United Kingdom ................. 424/54

Primary Examiner—Shep K. Rose
Attorney, Agent, or Firm—Robert L. Stone; Murray M. Grill; Herbert S. Sylvester

[57] ABSTRACT

Treatment of teeth by sorbing onto the tooth surfaces a combination of a cationic germicide and an anionic polymer.

31 Claims, No Drawings

TREATMENT OF TEETH

This invention relates to the treatment of the oral cavity. It is found that formation of calculus, or plaque, on the teeth can be significantly inhibited by sorbing onto the tooth surfaces a combination of a cationic germicide and an anionic polymer. In a preferred form of the invention there is applied to the tooth surfaces a very dilute (e.g. 0.15%) aqueous dispersion of a complex of the cationic germicide and anionic polymer. It is found that this complex is substantive to the teeth; that is, on contact with the teeth the complex is attracted to the teeth and is depleted from the dispersion, the complex being deposited onto the teeth under non-drying conditions without removing water or aqueous fluid from contact with the teeth. Thus the action is quite unlike the film formation which occurs on deposition of a solution or emulsion followed by evaporation of the solvent.

The surfaces of the teeth are largely composed of hydroxyapatite (calcium orthophosphate, basic) and the complex is found to be substantive to hydroxyapatite. For example, in tests in which wet saliva-coated disks of hydroxapatite are dipped into a highly dilute aqueous dispersion (e.g. of 0.15% or 0.01% concentration) made from carbon-14-labelled ingredients (i.e. (a) in one case, a combination of labeled cationic germicide and unlabelled anionic polymer and (b) in another case, an otherwise identical combination except that the germicide is unlabelled and the polymer is labelled) and then excess liquid is removed by blotting, the resulting dry disk is found to contain the labelled ingredients and the amount thereof present in the disk is found to increase with increasing immersion time. It is interestng that the amount of each ingredient sorbed by the disk from even a 0.01% dispersion is found to be appreciable even on one minute immersion and that a manifold increase in concentration (e.g. to 0.15%) results in a definite increase in amount sorbed (in the same time) which increase is, however, not nearly proportional to the increase in concentration. In the same tests it is also found that the germicide:polymer ratio in the treated disk is lower than said ratio in the dispersion used to treat the disks (e.g. below 1:1, such as 1:2, in the treated disk as compared to 2:1 in the dispersion). There are also indications of saturation and formation of an active germicidal monolayer at the surface of the disk.

The reasons for the effectiveness of the present invention are not clearly understood. Human enamel contains approximately 95% hydroxy apatite, the dentin contains 80% of the same and the rest are organic materials such as proteins. The hydroxy apatite has $Ca^{++}$, $OH^-$ and $HPO_4^=$ ions and protein has OH, $NH_2$ and SH groups in the amino acid constituents. All these can be brought into interaction with materials containing acid groups (e.g. carboxylate or sulfonate ions) through dative, ionic and hydrogen bonding. On the other hand, the same acid groups can be used to establish strong interaction between them and the positively charged cationic germicides. The ionic bonds will gradually undergo hydrolysis or ion-exchange and release the cationic germicide to exercise an antibacterial activity without raising the surface concentration of the cationic germicide to an undesirably high level.

Cationic germicidal materials are well known in the art. See, for instance the section on "Quaternary Ammonium and Related Compounds" in the article on "Antiseptics and Disinfectants" in Kirk-Othmer Encyclopedia of Chemical Technology 2nd edition (vol. 2 p. 632–635), incorporated herein by reference. Among the most common of these are germicidal quaternary ammonium compounds such as benzethonium chloride; others of this class (and generic formulas and descriptions thereof) are those mentioned, for instance, in U.S. Pat. Nos. 2,984,639, 3,325,402, 3,703,583, and 3,431,208 and British patent 1,319,396. Usually one of the substituents on the quaternary nitrogen has a chain length of some 8 to 18 carbon atoms. Other types are the amidines such as the substituted guanidines e.g. chlorhexidine and the corresponding compound having 2-ethylhexyl groups instead of chlorophenyl groups (Sterwin 904) and other bis-biguanides such as those described in German patent application P2,332,383 published Jan. 10, 1974 which sets forth the following formula:

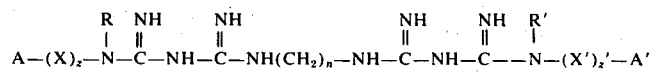

in which A and A' signify as the case may be either (1) a phenyl radical, which as substituent can contain up to 2 alkyl or alkoxy groups with 1 up to about 4 C-atoms, a nitro group or a halogen atom, (2) an alkyl group which contains 1 to about 12 C-atoms, or (3) alicyclic groups with 4 to about 12 C-atoms, X and X' as the case may be represent an alkylene radical with 1-3 C-atoms, z and z' are as the case may be either zero or 1, R and R' as the case may be represent either hydrogen an alkyl radical with 1 to about 12 C-atoms or an aralkyl radical with 7 to about 12 C-atoms, n is a whole number of 2 to inclusively 12 and the polymethylene chain $(CH_2)_n$ can be interrupted by up to 5 ether, thioether, phenyl- or naphthyl groups, or the pharmaceutically suitable salts thereof. The germicidal compound is preferably one which has a germicidal activity such that its phenol coefficient is well over 50, more preferably well above 100, such as above about 200 or more for S. aureus; for instance the phenol coefficient (A.O.A.C.) of benzethonium chloride (Hyamine 1622) is given by the manufacturer as 410, for S. aureus. THe cationic germicide will generally be a monomeric (or possibly dimeric) material of molecular weight well below 2,000, such as less than about 1,000. It is, however, within the broader scope of the invention to employ a polymeric cationic germicide. The cationic germicide is preferably supplied in the form of an orally acceptable salt thereof, such as the chloride.

Anionic polymers are also well known in the art. Preferably the polymer is one which is of the "linear" soluble type; that is, it is not so cross-linked as to be insoluble in a solvent. For Example, it may be soluble in water, when in its sodium or ammonium salt form, at least to the extent of the concentration in which it is employed (say 0.05%) but more preferably it is soluble at a higher concentration, such as 0.5%, 1% or 2%. See for instance the anionic polymeric materials described in U.S. Pat. Nos. 2,984,639, 3,325,402, the article on "Polyelectrolytes" in Vol. 10 of Encyclopedia of Polymer Science page pages 781 ff and particularly at pages 781, 782 and 784 listing various polyelectrolytes, the articles by Saito (Kolloid-Zeitschrift [1955] 143, 2, pp. 66–73 and Kolloid-Zeitschrift [1959] 165, 2 pp. 162–167) dealing with interaction of cationic compounds and anionic polymers. Good results have been obtained with anionic polymers of very high molecular weight, e.g. about 500,000 or 1,000,000 but materials of relatively low molecular weight, but preferably above 1,000, may also be employed, e.g. 2,000, 5,000 or 10,000. In one particularly preferred class the anionic polymer has ionizable carboxyl groups. In another it has sulfonic groups. A preferred type of polymer has its ionic substituents on a polymer chain which is hydrocarbon, preferably aliphatic hydrocarbon (e.g. a vinyl polymer).

Dispersions of the complexes may be produced by slowly adding a dilute solution of the cationic germicide to a dilute solution of the anionic polymer, and stopping the addition before the amount of cationic added is such as to from a precipitate with the anionic polymer. With slow enough rates of addition and good agitation one can produce dispersions having very small particle sizes, below 1 micron such as less than 0.7 microns, e.g. about 0.2 to 0.5 micron, or even dispersions which appear to be clear rather than cloudy.

The number of cationic units needed to form the dispersed complex is generally less than the number of anionic groups. For instance, a very suitable complex is formed by slowly adding (while maintaining the pH at, say about 5) benzethonium chloride to a copolymer of equal mols of methyl vinyl ether and maleic acid, using about 2/3 mol of the benzethonium chloride for each mol of maleic acid units. Since there are two carboxyls per mol of maleic acid, the 2/3 mol corresponds to ⅓ equivalent. However, the degree of ionization of the methyl vinyl ether-maleic acid copolymer is only about ⅝ at a pH of 5 (i.e. one carboxyl being unionized and the other being about 2/3 ionized). Thus it may be considered that the 2/3 mol of benzethonium chloride corresponds to a 1:1 equivalent ratio, i.e. about 1 equivalent of benzethonium per equivalent of ionized carboxyl. It is often preferable to use a partial salt of the anionic polymer, such as a water-soluble salt thereof with a cation of low molecular weight (e.g. a cation of molecular weight below 100, preferably monovalent, such as ammonium or alkali metal, like sodium or potassium). It will be understood that unionized carboxylic groups of the polymer may still be available for ionization and for ionic or other reactions, as at higher pHs or on contact with basic material such as hydroxyapatite.

The mol ratio (or equivalent ratio) of cationic germicide to anionic polymer can be decreased. Thus, particularly with cationic germicides of very high germicidal activity such as chlorhexidine, one preferably employs considerably lower ratios. For instance, a very effective complex may be made by slowly adding (at a pH of say about 7.5) chlorhexidene digluconate to the previously mentioned methyl vinyl ethermaleic acid copolymer, using about ⅓ mol or even 1/5 or ⅛ mol of chlorhexidine per mol of maleic acid in the copolymer. At the pH of 7.5 the copolymer is usually about 50% ionized, but the chlorhexidine digluconate is also only about 50% ionized, so that the equivalent ratio may be considered to be about the same as the mol ratio. The complexes of this type have been found to have very good storage stability and resistance to coagulation or precipitation on shaking. For cationic germicides of lower germicidal activity, higher mol ratios, and/or higher concentrations of the complex in the dispersion, may be preferred.

The concentration of the complex in the dispersion is preferably well below 2% and more preferably less than 1% and still more preferably below about 0.5% but above 0.01% such as about 0.05 to 0.3%. The concentration of the cationic germicidal component of the complex is preferably at least about 0.02% based on the weight of the dispersion (e.g. 0.25% or more, when chlorhexidine is the germicide calculated as the free chlorhexidine base, and 0.07% or more when benzethonium chloride is the germicide).

The pH at which the dispersion of the complex is employed will generally to within the range of about 4 to 9 more preferably about 5 to 7.5 or 8.

In particularly suitable aspects of the invention there is employed an aqueous dispersion of a complex of the cationic germicide and anionic polymer, in which dispersion the complex has one or more of the following characteristics. It resists breaking up on equilibrium dialysis against distilled water (see, for instance the tests in Ex. 7b below) when the dispersion is on one side of membrane of the type which permits passage of the cationic smaller molecules such as the germicide but not large molecules such as those of the molecular weight of the anionic polymer. It is decomposed, at least partially, on equilibrium dialysis against a solution of saliva salt (as in the test in Ex. 7b below). It is substantive to tooth surfaces but can be washed off by phosphate buffer solution (as in the test described in Ex. 7c below). It is substantive to tooth surfaces even in the presence of saliva (as in the test described in Ex. 2e and Ex. 7c below). In a serial dilution test (as described in Ex. 7d below) it has an MIC value of less than about 10, preferably below 5 and more preferably below 1 microgram of the cationic germicide component per ml, for S. Mutans (ATCC No. 19641). In a test in which the complex is sorbed onto saliva-coated hydroxy-apatite discs and then immersed in a suspension of Strep. sanguis (as in the test described in Ex. 7e below) it gives a kill percentage of at least about 70% (e.g. 100%). It is effective in a test for in vitro plaque formation (as described in Ex. 7f below). It is largely resistant to precipitation on centrifuging (as in the test described in Ex. 2b below). On passage through a filter having a controlled pore size of less than 1 micron, such as below 0.8 micron, the complex is still present in the dispersion and still active (as in the test described in Ex. 2f below).

The following Examples are given to illustrate this invention further. In this application all proportions are by weight unless otherwise indicated.

EXAMPLE 1 a. 0.3 gram of methyl vinyl ether-maleic anhydride copolymer (Gantrez 139) is solubilized in 60 cc of water at 60°C; this converts the anhydride groups to the corresponding carboxylic acid groups. Then a solution of 0.3 gram of benzethonium chloride in 60 cc of water is added gradually with stirring and the mixture is heated in a water bath at 60°C for 10 minutes. The mixture is a cloudy or milky aqueous dispersion.

b. 10 grams of hydroxyapatite powder (Bio Gel HTP, of Bio Rad Laboratories) is added to the aqueous dispersion produced in Example 1a and stirred while the mixture is maintained on the 60°C water bath for about 5 minutes. The solids are then filtered, washed on the filter with warm water and dried at room temperature. The dried powder is then analyzed for nitrogen content; it is found that the powder contains an amount of nitrogen corresponding to a content of about 2.5% of the benzethonium chloride, indicating that some 90% of the benzethonium chloride introduced into the solution has become attached to the hydroxyapatite.

c. One gram of the same anhydride copolymer as used in Example 1a is solubilized (to form the carboxylic acid copolymer) in 100 cc of water as 60°C. 4 grams of the hydroxyapatite is added and mixed as in Example 1b. An immediate reaction is noted, as indicated for instance by a change in the appearance of the solids. After filtering, washing on the filter, and drying (as in Example 1b) a product containing about 19% organic material is obtained. The organic content (largely protein) of the hydroxyapatite before treatment is very small (such as less than 1%, e.g. below 0.1%).

EXAMPLE 2 a. 0.5 g of methylvinyl ether-maleic anhydride copolymer (Gantrez AN-139) is added to 600 ml of water heated to 50°–60°C with stirring until substantially complete solution occurs (owing to hydrolysis of the anhydride groups). A solution of 1g of benzethonium chloride in 400 ml of water is added slowly with vigorous stirring while the temperature is maintained at 50°–60°C. Then dilute ammonium hydroxide is added to bring the pH to about 5 ½. The product is a milky dispersion.

b. When 30 grams of this dispersion is centrifuged, as described below, there is obtained a deposit of about 5 mg, representing about 10% of the solids in the dispersion. The centrifuging is effected by spinning the material in a centrifugal tube at 7500 rpm, equivalent to 6780 G, decanting the supernatant liquid, adding 20 ml of deionized water to the material remaining in the tube, spinning the tube again and again decanting the supernatant liquid, adding a small quantity of acetone (to aid in the evaporation of the water) and placing the tube in a dessicator to dry.

c. When a natural human tooth which has been cleaned by abrading the surface with pumice is dipped into an aqueous dispersion produced as in Example 2a for one minute and then placed in distilled water for 20 seconds, then stained with an 0.04% aqueous solution of Bromophenol Blue (a standard indicator for the presence of quaternary ammonium compound) and then rinsed with water, the tooth has a strong blue color, showing the substantivity of the dispersed material to the tooth material.

d. Aliquots of the dispersion produced as in Example 2a are adjusted to pHs of 5, 6, 7, and 8, respectively, by adding aqueous HCl or NH$_4$OH as required. Each of the resulting dispersions is tested for substantivity to teeth in the manner described below. Each is found to be substantive to the teeth.

The substantivity tests are carrier out with (1) cleaned (pumiced) etched human bicuspids and (2) cleaned unetched human bicuspids. In each case the teeth are immersed in the dispersion, then washed in running water for 1 minute (about ½ liter of water), stained with an 0.04% aqueous solution bromophenol blue and then rinsed in water. A blue stain remaining on the teeth indicates the presence of quaternary ammonium chloride on the teeth and thus indicates the substantivity of the dispersion. The cleaned, etched teeth are immersed in the dispersion for one minute, while the cleaned unetched teeth are immersed for 2 minutes. Cleaning is done with dental pumice; etching is carried out by immersion for 15 seconds in 2 N aqueous HClO$_4$ followed by washing with water.

e. When the dispersion is diluted 1:1 with fresh saliva (stimulated saliva) it is still substantive. In this test the tooth is immersed for 1 minute in the saliva-diluted mixture and then rinsed for 2 minutes in distilled water.

f. When the dispersion made as in Example 2a is filtered through filter paper (Whatman 50) and then through a Millipore filter having apertures 0.45 micron in diameter the filtered dispersion is found to be substantive to the tooth material although its action is slower and a longer time of immersion of the tooth in the dispersion is needed.

g. The dispersion produced as in Example 2a is tested for its anticalculogenic effects in beagle dogs. It is found that the animals show a greatly reduced tendency to calculus formation and any calculus deposit, when present, is of a different nature from that of the control in that it is easily removed by a rubber glove-covered finger.

EXAMPLE 3 a. 0.3 g of methyl vinyl ether-maleic anhydride copolymer (Gantrez 139) is solubilized in 60 ml of water at 60°C as in Example 1; then 0.5 g of octadecyl trimethyl ammonium bromide (MW 392), dissolved in 40 ml of water, is added with agitation to form a milky dispersion.

b. Example 3a is repeated except that 3-(1'-adamantane carboxamido)-propyl tetradecyl dimethylammonium bromide (MW 541) is used in place of the octadecyl trimethyl ammonium bromide.

c. Example 3a is repeated except that 0.4g of octyl trimethyl ammonium bromide (MW 242) is used in place of the 0.5g octadecyl trimethyl ammonium bromide.

d. Example 3a is repeated except that 0.6g of 1,14,bis-(p-chloro benzyl)-1,1,14,14-tetramethyl-1,14-diazonia tetradecane dibromide (a diquat, MW 703) is used in place of the 0.5 g octadecyl trimethyl ammonium bromide.

e. Example 3a is repeated except that dodecyl di (hydroxyethyl) benzyl ammonium bromide (Ciba Fungitex B, MW 368) is used in place of the octadecyl trimethyl ammonium bromide.

f. Example 3a is repeated except that 0.4 g of benzalkonium chloride (MW 310) is used in place of the 0.5 g octadecyl trimethyl ammonium bromide.

g. Example 3a is repeated except that cetylpyridium chloride (MW 358) is used in place of the octadecyl trimethyl ammonium bromide.

h. Example 3a is repeated except that 0.8 g chlorhexidine digluconate (MW 898) is used in place of the 0.5 g octadecyl trimethyl ammonium bromide.

i. Example 3a is repeated except that 0.3 g of 2-(ethyl thiocarbamyloxy)-ethyl dimethyl dodecyl ammonium bromide is used in place of the 0.5g octadecyl trimethyl ammonium bromide.

j. Example 3a is repeated except that 0.3 g of "Bionol", n-alkyl (C$_{12}$ 5%, C$_{14}$ 60%, C$_{16}$ 30%, C$_{18}$ 5%) benzyl dimethylammoniumchloride is used in place of the 0.5g octadecyl trimethyl ammonium bromide.

k. Example 3a is repeated except that 0.3 g of cetyl pyridiniumchloride is used in place of the 0.5 g octadecyl trimethyl ammonium bromide.

l. Example 3a is repeated except that 0.3 g of "Onyxide 3000", n-Alkyl ($C_{12}$ 40%, $C_{14}$ 50%, $C_{10}$ 10%) dimethylbenzylammonium sacharinate is used in place of the 0.5 g of octadecyl trimethyl ammonium bromide.

In each case the dispersion reacts with hydroxyapatite powder and with tooth surfaces, as indicated by the following tests.

In one test one gram of powdered hydroxyapatite (Biorad) is mixed with 100 ml of the dispersion at room temperature for 2 minutes and the powder is then filtered off and washed with 100 to 500 ml of deionized water and then air dried. A drop of a 0.04% solution of Bromophenol Blue is placed on the treated powder and a blue color is observed.

In another test extracted and cleaned human teeth are immersed in the dispersion for 2 minutes at a temperature of 35–38°C then dipped in water several times and dried in air at room temperature. The teeth (still dry) are then placed in a 3% aqueous solution of Todd Hewitt Broth (BBL) in a test tube (previously sterilized by steam) along with a platinum loop-full of S. Mutans from a freshly grown culture thereof, and the test tube is incubated at 37.5°C. along with the control. The clarity of the solution is checked for the inhibition of bacterial growth. In each case the bacterial growth is inhibited for at least 1 day.

In the above Example 3a through l the mole ratio of the bactericidal compound to maleic acid (present, in combined form, in the copolymer) ranges by simple calculation, from about 1/3:1 to almost 1:1. The ratio can also be expressed on the basis of number of salt groups present in the bactericidal compounds (some are di-salts, i.e. Example 3d and h); in the above Example 3a through l the ratio of the number of salt groups of the bactericidal compound to the number of maleic acid units is in the range of about 1/2:1 to about 1:1.

EXAMPLE 4 a. A copolymer of equal mols of methyl vinyl ether and maleic anhydride (Gantrez 119, having a molecular weight of 250,000) is added slowly to water with continuous stirring at 50–60°C. to form a 0.1% solution of polymer. To 500 ml of the resulting solution there is added a few drops of dilute $NH_4OH$ solution to bring the pH to 7–7.5. To this solution chlorhexidine digluconate (in the form of a 20% W/V aqueous solution thereof) is added slowly with continuous stirring. The amount of chlorhexidine digluconate salt is equivalent to about 0.1 gram of chlorhexidine free base. During the mixing, a few drops of dilute $NH_4OH$ solution is added to maintain the pH at 7–7.5. The weight ratio of chlorhexidine (calculated as free base) to polymer is about 1:1.

b. Example 4a is repeated, substituting Gantrez 139 (500,000 molecular weight) for the Gantrez 119.

c. and (d) Examples 4a and b, respectively, are repeated, but the proportion of polymer is decreased so as to give a chlorhexidine:polymer ratio of 2:1 and a concentration of combined chlorhexidine in the resulting aqueous dispersion of about 0.05%.

e. and (f) Examples 4a and b, respectively, are repeated, but the proportion of polymer is increased so as to give a chlorhexidine:polymer ratio of 1:2 and a concentration of combined chlorhexidine in the resulting aqueous dispersion of about 0.05%.

In each case the liquid is a translucent to milky dispersion. Ultraviolet absorption and turbidity studies of the liquids yield the following results, in which "C" stands for "chlorhexidine", "P" for "polymer", "O.D." for optical density and "A" for absorption. Turbidity is measured with B & L Spectronic 20. The concentrations and pHs specified are those in the dispersions, but for the U.V. absorption test all are diluted 100X. Where two figures are given (for the turbidity) they are results on different batches.

| Weight ratio C:P | Concentration of components in dispersion (%) | | pH | Turbidity A 610 mμ | Ultraviolet absorption Peak 1 | | Peak 2 | |
|---|---|---|---|---|---|---|---|---|
| | C | P | | | O.D. | mμ | O.D. | mμ |
| "Gantrez 119" | | | | | | | | |
| | 0.1 | 0 | 6.8 | | 0.58 | 233 | 0.57 | 256 |
| 1:1 | 0.1 | 0.1 | 7.2 | 0.72 | 0.38 | 234 | 0.43 | 265 |
| 2:1 | 0.1 | 0.05 | 6.7 | 0.56 0.62 | 0.26 | 234 | 0.28 | 266 |
| 1:2 | 0.1 | 0.2 | 8.0 | 0.85 | 0.27 | 234 | 0.29 | 266 |
| | 0.05 | 0 | 7.2 | 0.00 | 0.26 | 233 | 0.26 | 258 |
| 1:1 | 0.04 | 0.05 | 6.9 | 0.36 0.26 | 0.25 | 234 | 0.28 | 265 |
| 2:1 | 0.05 | 0.025 | 6.7 | 0.21 0.23 | 0.18 | 234 | 0.19 | 265 |
| 1:2 | 0.06 | 0.1 | 7.0 | 0.29 | 0.28 | 234 | 0.30 | 265 |
| "Gantrez 139" | | | | | | | | |
| | 0.1 | 0 | 6.8 | | 0.58 | 233 | 0.57 | 256 |
| 1:1 | 0.1 | 0.1 | 7.0 | 0.85 0.85 | 0.39 | 233 | 0.43 | 265 |
| 2:1 | 0.1 | 0.05 | 7.0 | 0.58 0.64 | 0.18 | 233 | 0.19 | 265 |
| 1:2 | 0.1 | 0.2 | 7.8 | 1.25 | 0.21 | 233 | 0.21 | 265 |
| | 0.05 | 0 | 7.2 | 0.00 | 0.32 | 233 | 0.32 | 258 |
| 1:1 | 0.05 | 0.05 | 7.0 | 0.31 | — | — | 0.26 | 265 |
| 2:1 | 0.05 | 0.025 | 7.0 | 0.22 0.23 | — | — | 0.20 | 265 |
| 1:2 | 0.05 | 0.10 | 6.7 | 0.48 | 0.25 | 233 | 0.27 | 266 |
| | 0.05 | 0 | 7.2 | 0.00 | 0.26 | 233 | 0.26 | 258 |

It will be seen that the polymer-chlorhexidine combinations show a decided shift in the second of the two peaks (absorption maxima) as compared to chlorhexidine per se. (The lower U.V. optical density and the turbidity of the polymer-hexidine combinations is an indication of their colloidal nature; i.e. the dispersions contain finely suspended particles of the combination.)

The combination is substantially insoluble in such solvents as acetone, absolute ethanol, 95% ethanol, 5N NaOH solution, dimethylformamide, ethyl acetate, acetonitrile, benzene, tetrahydrofuran, petroleum ether, dimethylsulfoxide, hexane and ethyl ether, but soluble (e.g. in 0.05 or 0.1% concentration) in 1N aqueous HCl.

When the dispersions containing (I) 0.05% combined chlorohexidine and 0.025% Gantrez-119 or (II) 0.1% combined chlorhexidine and 0.1% Gantrez-119 are acidified (with 1N aqueous HCl) to pH 2-3 they tend to form larger aggregates or clumps; lowering the pH (in the same way) to 1 causes the material to become almost completely dissolved forming a clear solution. Raising the pH thereafter causes reappearance of the colloidal particles.

EXAMPLE 5

Example 4a is repeated using ethylene-maleic anhydride copolymer (1:1 mol ratio of molecular weight about 10,000, Monsanto EMA No. 1103) in place of the Gantrez resin, in the following proportions based on the total weight of the resulting dispersion (again, "C" stands for chlorhexidine, calculated as the free base, and "P" stands for polymer):

| | | |
|---|---|---|
| (a) | 0.1% C | 0.1% P |
| (b) | 0.1% C | 0.05% P |
| (c) | 0.05% C | 0.05% C. |

All these are colloidal dispersions of fine particles.

EXAMPLE 6

Benzethonium chloride is combined with various water-soluble acid-containing copolymers (listed below) in the manner described in Example 2 using the weight ratios of polymer to benzethoniumchloride tabulated below.

| | Acidic Monomer ("A") | Co-Monomer ("B") | Mol Ratio A:B | Weight Ratio Polymer: benzethonium chloride |
|---|---|---|---|---|
| (a) | Acrylic Acid | Methyl methacrylate | 1:1 | 1:1 |
| (b) | Acrylic acid | Hydroxyethyl methacrylate | 1:1 | 1:1 to 2:1 |
| (c) | Acrylic acid | methyl acrylate | 1:1 | 1:1 |
| (d) | Acrylic acid | Ethyl acrylate | 1:1 | 1:1 |
| (e) | Acrylic Acid | Isobutyl vinyl ether | 1:1 | 1:1 |
| (f) | Acrylic acid | N-vinyl-2-pyrolidone | 1:1 | 2:1 to 3:1 |
| (g) | Sodium vinyl sulfonate | Ethyl acrylate | 1:2 | 3:1 to 4:1 |
| (h) | Sodium vinyl sulfonate | Hydroxyethyl methacrylate | 1:2 | 3:1 to 4:1 |
| (i) | Sodium vinyl sulfonate | N-vinyl-2-pyrollidone | 1:2 | 3:1 to 4:1 |
| (j) | maleic anhydride | Ethyl acrylate | 1:1 | 1:1 |
| (k) | maleic anhydride | Hydroxyethyl methacrylate | 1:1 | 1:1 to 2:1 |
| (l) | maleic anhydride | N-vinyl-2-pyrrolidone | 1:1 | 2:1 to 5:1 |
| (mL | maleic anhydride | Ethylene | 1:1 | 0.5:1 to 1:1 |

In each of j, k, l and m the maleic anhydride copolymer is completely hydrolyzed to its acid form before combining it with the benzethonium chloride. Each product is tested for its substantivity to hydroxyapatite by mixing hydroxyapatite powder therewith (e.g. one gram of powder to 100 ml of a dispersion containing 0.1% of the benzethonium chloride in combined form) and stirring at a temperature of about 38°C for about 5 minutes, then filtering, washing the solids on the filter with warm water and drying the solids at room temperature. When a drop of 0.04% aqueous solution of Bromophenol Blue is applied to the dried solids a blue color develops (which, in each case, remains on rinsing with water) showing that quaternary ammonium compound is bonded to the hydroxyapatite.

EXAMPLE 7 a. One gram of methyl vinyl ether/maleic anhydride copolymer (Gantrez-139, M.W. 500,000) is added slowly to 900 ml of water at 50°–60°C. Five drops of 1N HCl is added to hasten hydrolysis, and volume is adjusted to 1 liter. To 500 ml of this 0.1% solution of the polymer is added a few drops of dilute 3N ammonium hydroxide to bring the pH to 4.0. 500 ml of a 0.2% solution of benzethonium chloride in water is then added slowly at 40°–45°C with a continuous stirring. Then the pH is adjusted to 5 to 5.5 with $NH_4OH$. The resulting liquid is a milky dispersion of a complex of the cationic germicide and anionic polymer.

b. Samples of the resulting complex-containing dispersion are placed into dialysis sacs and subjected to equilibrium dialysis for 24 hours at room temperature (e.g. 25°C) against the following materials (which surround the sac):

A. deionized water (B) phosphate buffer solution (0.1M, pH 7.0) (C) saliva salt solution. The sacs are each made of a membrane which permits passage (dialysis) of small molecules or ions through it but which prevents passage of large molecules (or ions) of molecular weight about 10,000 or more. The surrounding solution is then tested for the presence of quaternary ammonium compound, which would indicate breaking up of cationic-anionic complex of the initial dispersion and migration of the cationic material through the membrane. It is found that only in case C is there substantial dissociation of the complex. Thus after the 24 hours the complex is some 90% dissociated in case C and some 0% dissociated in cases A and B. The saliva salt solution has the following composition: $CaCl_2 \cdot 2H_2O$ 227.8 mg; $MgCl_2 \cdot 6H_2O$ 61.0 mg; NaCl 1.017g;

$K_2CO_3$ 504.5 mg; $Na_2HPO_4$ 107.9mg; $NaH_2PO_4$ 237.1 mg; distilled water to make 1 liter; pH adjusted to 7.2 by bubbling in $CO_2$ or adding 0.1N HCl.

c. To evaluate the attachment of the complex to tooth surfaces, a test is carried out using Bromophenol Blue, which reacts with the cationic germicide to form an insoluble blue complex. In this test extracted human teeth (which have previously been cleaned and pumiced and whose roots have been protected with wax) are first dipped into clarified saliva for 30 seconds; then rinsed in deionized water to remove excess saliva; then dipped for 30 seconds in the complex-containing dispersion produced in a above; then rinsed in deionized water to remove excess dispersion; then stained by dipping them (for 30 seconds) into a 0.05% solution of Bromophenol Blue in deionized water; and then rinsed in deionized water to remove excess dye. The teeth are found to have a moderately blue color. When the same test is repeated except that the teeth treated with the complex (and rinsed to remove surface excess) are given two similar rinsings, but with 0.05M phosphate buffer having a pH of 7.0 (instead of water), before being dipped into the dye solution the teeth are not colored when treated with the dye solution. In the rinsing steps used herein the tooth is immersed in the rinse medium without agitation. The procedure is carried out at room temperature.

The phosphate buffer solutions are mixtures of solutions of monobasic sodium phosphate and dibasic sodium phosphate in water. One may start with 0.2M stock solutions of each salt. To make a 0.1 N pH 7.0 buffer solution one may mix 39 ml of the monobasic stock solution and 61 mol of the dibasic stock solution and then dilute to 200 ml with water. For the 0.05 N solution the same mixture is diluted to 400 ml.

d. Tests for antibacterial activity by a two fold serial dilution test against the following organisms are made with the complex-containing dispersion produced in a above, with the following results:

| Organism | Minimum Concentration (in micrograms of combined benzethoniumchloride per ml) needed to give complete inhibition of growth. |
|---|---|
| Staph. aureus | 0.4 |
| Strep. mutans | 0.053 |
| Strep. sanguis | 0.313 |
| Actonomyces naeslundii | 25.0 |
| Candida albicans | 0.4 |
| E. coli | 50.0 |
| P. aeruginosa | 50.0 | e. The attachment of the complex to hydroxyapatite and the antibacterial properties of the treated hydroxyapatite are tested as follows. Hydroxyapatite discs (circular, 16 mm diameter, 1 mm thick, 0.250g in weight, made by pressing hydroxyapatite powder into disc form at high pressure (e.g. 100,000 psi) and sintering the disc at 800°C, are pre-sterilized, coated with clarified saliva, and then immersed for 1 minute at room temperature in a sample of the complex-containing dispersion produced in a above. The treated discs are then immersed in a bath of 2 ml of a washed suspension of Strep. sanguis (7.5 × $10^6$ organisms per milliliter). The number of organisms killed after 5 minutes contact with treated discs is evaluated by plate count. It is found that all organisms are killed. When the same test is repeated except that the treated disc (after rinsing in water to remove surface excess) is given two rinsings with 0.05M phosphate buffer having a pH of 7.0 before being subjected to the bacterial suspension, the percent kill is still 100%. However when three rinsings, instead of two, are used the percent kill drops to zero. As previously indicated, in the rinsing steps used herein the disc is immersed in the rinse medium without agitation.

f. Tests are made of the ability of the complex to inhibit in vitro plaque formation on the surfaces of clean teeth by Strep. mutans as well as the effects on a preformed intact plaque (Strep. mutans) on the surfaces of the teeth. Extracted human teeth are cleaned, pumiced and sterilized with steam. The teeth coated with saliva are then dipped into a sample of the complex-containing dispersion produced in a above for 1 minute at room temperature and then transferred to sucrose broth (Trypticase soy broth supplied by Baltimore Biological Labs. containing 5% sucrose) which is preinnoculated with Strep. mutans, so as to comprise 4×$10^8$ cells per ml. Plaque formation is observed over a period of 3–4 days against control teeth which have been treated with sterile distilled water (or buffer). In another test, plaque is allowed to form (for 48 hours at 37°C) on the surfaces of cleaned and pumiced teeth in the same preinnoculated sucrose broth containing Strep. mutans. The pre-grown plaque is then immersed into a sample of the complex-containing dispersion produced in a above (for one minute). The teeth carrying the plaque are then transferred to a sucrose broth containing 1 mg/100 ml of bromocresol green indicator and incubated at 37°C anaerobically for 18 hours. An anti-bacterial compound is considered effective if the indicator does not turn yellow (which begins when pH reaches 5.5) and there is no further growth of the plaque as judged by the increase in turbidity. It is found that on the clean teeth, plaque formation is prevented. On the pre-grown plaque, acid formation and plaque growth are effectively inhibited.

g. The tooth staining characteristics of the complex are tested on cleaned extracted human teeth by dipping the teeth successively into saliva (with or without the complex) and various stain-producing liquids and repeating the same sequence (automatically) until a control shows a noticeable stain, which resists hard brushing with a toothbrush and a commercial toothpaste for some 60 seconds. The sequence of dipping is (1) clarified saliva (2) aqueous tea extract (3) aqueous tobacco extract (4) aqueous 0.5% solution of dextran of microbial origin. Each immersion is followed by 30 seconds drying under a stream of air at room temperature and then immersion into the next liquid of the sequence. The control test uses saliva without additive. The test of the complex uses, in one case, a mixture of about half saliva and half complex-containing dispersion produced in a above; in another case, the tooth is dipped into the complex for 30 seconds between steps 1 and 2 above. Substantially the same degree of staining is produced in the presence of the complex as in the control.

h. Tests are made of in vivo plaque formation in dogs whose teeth have been treated with the complex. The following results are obtained:

| Compound | 0 | 1 | 3 | 5 | 7 | 9 | 11 | 13 | 15 |
|---|---|---|---|---|---|---|---|---|---|
| Plaque Scores (Average of 4 dogs/group)* TREATMENT WEEKS | | | | | | | | | |
| Control (distilled water) | 2.00 | 2.40 | 2.43 | 2.47 | 2.56 | 2.41 | 2.47 | 2.50 | 2.13 |
| Dispersion of complex (produced in a above) | 1.97 | 1.78 | 1.50 | 1.59 | 1.62 | 1.53 | 1.59 | 1.53 | 1.30* |

Scoring:
1 = plaque present on any ¼ surface of the tooth
2 = plaque present on any ½ surface of the tooth
3 = plaque present on any ¾ surface of the tooth
4 = plaque present on entire surface of the tooth

*The plaque reductions are significant at 99.9 percent confidence level. All animals survive the test.

The animals used are registered Beagle dogs at least 6 to 8 months old, for good health and have not received oral treatment for at least three weeks prior to the start of the study. The animals are anesthetized and receive a complete dental prophylaxis; a disclosing solution is used to insure the complete removal of all plaque and calculus. The dogs thereafter receive the following diet exclusively: ground Purina Dog Chow soaked in water for at least 2 hours to form a soft mush. In addition, each animal receives daily, approximately 1/2 can of ground horse meat or ground beef (no chunks). No hard substances are permitted.

The animals are treated once daily with the test solutions using a gentle spray over all surfaces of the dentition. The treatment is continued for at least five days per week.

Each animal is examined initially, after one week and at biweekly intervals thereafter, for plaque, gingivitis, calculus and stain. The experiment lasts for 15 weeks.

EXAMPLE 8

The following materials are found to have an antibacterial effect against S. Mutans and S. Sanguis.

a. Hydroxyapatite powder treated with a dispersion of the complex as in Example 1b;

b. Hydroxyapatite powder treated as follows:

0.3 gram of ethylene-maleic anhydride copolymer (EMA Grade 61, Monsanto) is solubilized in 60cc water (converting the anhydride groups to acid groups) and then introduced into the solution of 0.15g of the quaternary ammonium chloride used in Example 1. This is heated at 60°C for twenty minutes. About 40cc warm water is added and 10g hydroxyapatite powder is mixed and heated on water bath for about five minutes. After that product is filtered, washed with 200cc water and dried. Nitrogen analysis shows that the product contains 1.2% of the quaternary. This shows that about 85% of the quaternary has been attached.

c. Hydroxyapatite powder treated as follows: Example 8b above is repeated except that 2-(ethyl thiocarbamyloxy) ethyl dimethyldodecyl ammonium bromide is used as the cationic germicide. Nitrogen analysis shows that 1:25%, or more than 90% of the quaternary ammonium chloride, has been attached to the hydroxyapatite.

EXAMPLE 9

A 0.1% solution of Gantrez 139 is made as in Example 1 except that a few drops of dilute HCl are added to adjust the pH of the solution to about 3. Then, to different 10ml samples of the solution, 10 ml each of 0.2% solutions of the following lowing cationic germicides are added; thereby forming dispersions which are clear in appearance. They are then adjusted to pH 5 by addition of a few drops of dilute ammonium hydroxide and becomes slightly milky. The resulting dispersions are used to treat extracted human teeth by immersing the teeth (after cleaning and pumicing and with or without them coating with wet saliva) into the dispersion for 2 minutes at 38°C, washing with running deionized water and then air drying (at room temperature). The teeth are then immersed in a 3% aqueous solution of Todd Hewitt Broth (BBL) in a test tube (previously sterilized by steam) along with a platinum loop-full of S. Mutans from a freshly grown culture of S. Mutans, and the test tube is incubated at 37.5°C. along with the control. The clarity of the solution is checked every day for the inhibition of bacterial growth. After four days no bacterial activity is seen. The cationic germicides used in this Example are:

a. benzethonium chloride,
b. cetyl pyridinium chloride,
c. the diquaternary compound of Example 3(d) above.

EXAMPLE 10

To 10 ml samples of a 1.0% solution of hydrolyzed copolymer of N-vinyl-2 pyrollidone and maleic anhydride (in 1:1 mol ratio) at a pH of 6 there are added 10 ml samples of 0.2% solutions of the following cationic germicides. Tests with hydroxyapatite and on extracted human teeth, as described in earlier Examples, show high bactericidal effectiveness. The germicides are a. benzethonium chloride,
b. cetyl pyridiniumchloride.

In all cases, when water is mentioned in the above Examples, "deionized water" is intended. The saliva employed is sterile clarified saliva made by centrifuging saliva (obtained on chewing a standard White Laboratories chewing gum base) at about 1200 G and then sterilizing (with ultraviolet at 2 cm distance) the supernatant liquid. In coating with the clarified saliva the object to be coated is immersed (e.g. horizontally in the case of the disks) in this supernatant liquid in a vessel and the liquid is then withdrawn from the vessel, as by aspirating it out of the vessel, thus leaving a film of the saliva adhering to the object.

The benzethonium chloride mentioned above is a well known germicide having the formula:

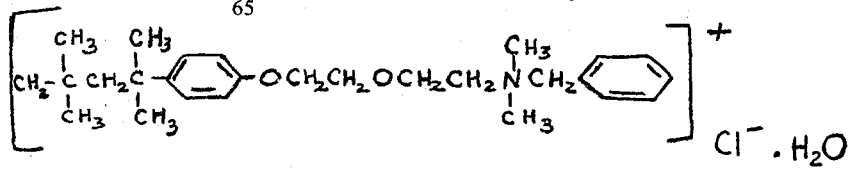

The pH of a 1% aqueous solution thereof is given in the literature as between 4.8 an 5.5. Its critical micelle concentration in water is about 0.06%.

Chorhexidine is also a well known germicide having the formula:

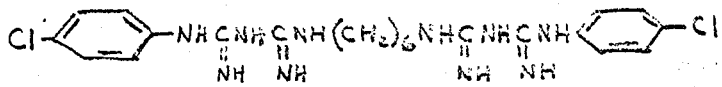

The pH of a 0.1 % solution of its digluconate salt is about 6.9 . The free chlorhexidine base is quite insoluble in water.

When a 0.05% solution of the vinyl methyl ether-maleic acid copolymer (of about 500,000 M.W.) is titrated with 0.02308 N aqueous sodium hydroxide and the pH is measured, a neutralization curve having two inflection points is obtained, the curve being approximately defined by the following data in which "ml" represents ml of the 0.02308N solution of base:

| ml: | 0 | 0.5 | 1.0 | 1.5 | 1.8 | 2.0 | 2.3 | 2.5 | 3.0 |
|---|---|---|---|---|---|---|---|---|---|
| pH: | 3.5 | 4.0 | 4.6 | 5.0 | 5.2 | 5.3 | 5.5 | 5.8 | 6.4 |
| ml: | 3.3 | 3.5 | 3.75 | 4.0 | 4.3 | 4.5 | 4.75 | 5.0 | 5.5 |
| pH: | 7.1 | 7.6 | 8.2 | 8.5 | 8.7 | 8.9 | 9.1 | 9.3 | 9.6 |
| ml: | 6.0 | 6.5 | 7.0 | 7.5 | 8.0 | 9.0 | 10.0 | | |
| pH: | 9.9 | 10.1 | 10.3 | 10.5 | 10.7 | 10.8 | 11.0 | | |

The anionic polymer is preferably one which itself has an affinity for, or is substantive to, hydroxyapatite. Thus, in the previously described test (in which disks of hydroxyapatite are dipped into an aqueous medium to test substantivity) the following data is obtained for a labeled copolymer solution, of hydrolyzed Gantrez 131 without cationic germicide: after exposure to a 0.1% solution of the polymer for 1 minute, about 5.1 micrograms of the polymer are present in the disk; on 2, 5 and 12 minute exposures to the same solution the figures are about 7.8, 14.2 and 19.8 micrograms respectively; when a 0.01% solution of the polymer is used and the exposure is for 1 minute, about 1.3 micrograms of polymer are present in the disk. The test is at room temperature.

In the preferred anionic polymers the distance between adjacent carboxyl groups is preferably less than 7 Angstrom units. The cationic germicide is preferably supplied to the complex-forming reaction in a solution in which it forms micelles, thus providing solved aggregates (e.g. micelles) of high positive charge density.

While particularly good results, in terms of plaque inhibition and other effects in the oral cavity, such as on tooth surfaces, have thus far been obtained by applying simple cloudy aqueous dispersions of the complex, it will be understood that it is within the broader aspects of the invention to incorporate the cationic germicide and anionic polymer into oral compositions generally, such as clear or cloudy mouth rinses and transparent or opaque toothpastes, and that in such compositions the complex may be formed in situ, e.g. during the preparation of the composition or even on dilution in the mouth, or no presently detectable complex may be formed but the cationic germicide and anionic polymer may act cooperatively on, and both be sorbed onto, the tooth surfaces.

Oral preparations containing combination of cationic germicide and anionic polymer will generally contain an added sialologue or flavoring material, e.g. in amount in the range of about 0.02 to 2% such as about 0.02 to 0.5 or 1%. Examples of suitable flavoring constituents include the flavoring oils, e.g., essential oils such as oils of spearmint, peppermint, wintergreen, sassafras, clove, sage, eucalyptus, marjoram, cinnamon, lemon and orange, as well as methylsalicylate and other components, e.g. menthol, thymol, cineol, cinnamic aldehyde, etc. Suitable sweetening agents include sucrose, lactose, maltose, sorbitol, sodium cyclamate and saccharine. Many of the flavoring agents are immiscible with, or do not disperse readily in, water and, for mouth rinses, it is often desirable to add them as solutions in water-miscible solvent (e.g. ethanol) to the dispersion. The weight of ethanol or other organic solvent present in the finished product is generally less than the weight of water (e.g. a water:solvent ratio more than about 2:1, and preferably more than 5:1, such as about 6:1 or 10:1).

In a toothpaste, which usually contains some 5 to 50% of a finely divided insoluble dental abrasive (generally as particles of average particle size of, say, 2 to 20 microns), the flavoring agent may be sorbed onto the surfaces of the abrasive particles.

Surprisingly, it is found that an unflavored aqueous dispersion of the complex itself has a relatively bland taste as compared to the harsh taste of a solution of the corresponding cationic germicide alone.

It will be understood that, as is conventional, the oral preparations are to be sold or otherwise distributed in suitably labelled packages. Thus a jar of mouthrinse will have a label describing it, in substances, as a mouthrinse or mouthwash and having directions for its use; and a toothpaste will usually be in a collapsible tube, or other squeeze dispenser for metering out the contents, having a label describing it, in substance, as a toothpaste or dental cream.

In oral compositions such as mouthrinses and toothpastes a surfactant is often present, e.g. to promote foaming. It will be understood that it is preferable to employ nonionic surfactants rather than their ionic counterparts. Examples of water-soluble nonionic surfactants are condensation products of ethyleneoxide with various compounds reactive therewith having long hydrophobic chains (e.g. alphatic chains of 12 to 20 carbon atoms) which condensation products ("ethoxamers") have hydrophobic polyoxyethylene moieties, such as condensation products of ethylene oxide and fatty acids, fatty alcohols, fatty amides, including alcohols such has sorbitan mono-stearate or polypropyleneoxide.

In the preparation of a mouth rinse the other ingredients, e.g. alcohol, flavor, glycerol (or other polyhydric alcohol such as sorbitol), and color may be mixed together and then blended with an aqueous dispersion of the complex of cationic germicide and anionic polymer; or said other ingredients may be added successively to said dispersion; or an aqueous mixture containing dissolved anionic polymer, together with some or all of the other ingredients, may be prepared and an aqueous solution of the cationic germicide may be added thereto.

Toothpastes conventionally contain an abrasive powder in a dental vehicle, to form a creamy mass preferably of such consistency as to be extracted from a collapsible toothpaste tube. The dental vehicle generally comprises a liquid such as water, glycerol, sorbitol, propylene, glycol, polyethylene glycol (e.g. of average molecular weight 400, etc.) or the like, including suitable mixtures thereof. It is usually advantageous to use a mixture of both water and a humectant, such as glycerine, sorbitol, propylene glycol or the like. The total liquid content is generally about 20–90% or more by weight of the toothpaste. In transparent and translucent toothpastes the liquid content of the toothpaste may be about 20–90% or more by weight while in opaque toothpastes the total liquid content is usually about 20–50%. The dental vehicle of a toothpaste usually also contains a gelling agent, such as the natural and synthetic gums and gum-like materials, including such polymers as Irish moss, hydroxymethyl carboxyethyl cellulose, polyvinyl pyrrolidone starch and the like, e.g. in an amount up to about 10% by weight of the toothpaste and preferably in the range of about 0.3–5% by weight. In the practice of this invention, in which an anionic polymer is present to interact or cooperate, with the cationic germicide, any gelling agent in the toothpaste is preferably of the essentially nonionic type such as hydroxyethyl cellulose, methyl cellulose, starch, polyvinyl alcohols, etc., in amounts as stated above. The abrasives conventionally employed in toothpastes include such materials as insoluble phosphate salts, such as insoluble sodium methaphosphate, insoluble potassium metaphosphate, calcium pyrophosphate, magnesium orthophosphate, trimagnesium orthophosphate, tricalcium phosphate, dicalcium phosphate dihydrate, anydrous dicalcium phosphate and the like, calcium carbonate, magnesium carbonate, hydrated alumina (e.g. alpha alumina trihydrate), dry silica gel, zirconium silicate and aluminum silicates, including calcined aluminum silicate and various mixtures of abrasives, the proportion being say, from 5% to 60% or more. In the practice of this invention alpha alumina trihydrate, alone or in admixture with say, calcined alumina, is a preferred abrasive. The toothpastes generally contain a surfactant, e.g. in amount in the range of about 0.05–5% by weight, such as about 1–3% of the dentifrice; as previously indicated in the practice of this invention it is preferred that any added surfactant be of the nonionic type, to avoid possible undesirable interactions with the cationic germicide and anionic polymer.

It is also within the broader scope of the invention to include, in the oral composition, a fluorine-containing compound having a beneficial effect on the care and hygiene of the oral cavity, such as fluorine compounds which tend to diminish enamel solubility in acid or otherwise aid in protecting the teeth agains decay. Examples of fluorine compounds are sodium fluoride, stannous fluoride, potassium fluoride, potassium stannous fluoride ($SnF_2 \cdot KF$), sodium hexafluorostannate, stannous chlorofluoride, sodium fluorozirconate and sodium monofluorophosphate. These materials, which dissociate or release fluorine containing ions in water, may be present in an effective but non-toxic amount, usually within the range to provide about 0.01 1% of dissolved fluorine.

A mouthrinse may be prepared, by mixing the following ingredients:15% of flavored 95% ethanol (i.e. 95/5 ethanol/water mixture containing about 1.45% thereof [i.e. about 0.22% of the total mouthrinse composition] of essential oils as flavoring and denaturant, said essential oil comprising about one-half methonal, about 20% methyl salicylate and the balance other essential flavoring oils); 3% of nonionic surfactant (Pluronic FN8, a polyoxyethylene polyoxypropylene block copolymer); 10% of glycerol; 0.1% of benzethonium chloride; 0.05% of 1:1 copolymer of methyl vinyl ether and maleic acid (added as a 1% solution of hydrolyzed Gantrez 139, the solution pH having been adjusted to about 5.5 with ammonium hydroxide); 0.02% of sodium saccharinate; 0.0006% of dye (a mixture of about equal parts of FD&C Blue No. 1 and FD&C Yellow No. 5 added as a freshly made 0.1% solution thereof in water); and the balance water. The ingredients are blended by adding the surfactant to the alcohol, then adding the solution of polymer, after which the glycerine is added, then the water, then the benzethonium chloride, then the sodium saccharin, then the dye; the mixture is then filtered through two layers of filter paper. Its pH is about 5.7. In general one may use, for instance, about 5 to 25% of the alcohol (e.g. about 11–17%), about 0.5 to 4% of the nonionic surfactant (e.g. about 1–5%), about 3 to 20% glycerol (e.g. about 7 to 12%), about 0.02 to 0.2% cationic germicide (e.g. about 0.05 or 0.075 to 0.1%), about 0.05 to 0.1% anionic polymer (e.g. about 0.025 to 0.05%), about 0.01 to 0.04% sodium saccharin and up to about 0.01% dye.

A toothpaste may be prepared by mixing the following ingredients, in the order given: 22% of glycerol; 1% of nonionic gum (hydroxyethyl cellulose, Natrosol 250M); 0.2% of sodium saccharin, 0.25% of 1:1 copolymer of methyl vinyl ether and maleic acid (added as a 1.425% solution of hydrolyzed Gantrez 139 in water, the pH of the solution having been adjusted to 3.9 with ammonium hydroxide); to the resulting gel, then, 32% of alpha alumina trihydrate powder of dentifrice grade (a conventional dental abrasive) and 20% of thin flakes of calcined alumina of about 3 micron particle diameter ("Microgrit", described in U.S. Pat. No. 3,121,623), about 1% flavor (essential oils); the balance is water, which is preferably added to the gel before the addition of the dental abrasives. The resulting mixture is deaerated in conventional manner. In general the proportion of glycerol or other humectant (such as 70/30 sorbitol-water mixture) is in the range of about 20–75%, e.g. about 20 to 50%; the proportion of gelling agent (preferably of the nonionic type) is in the range of about 0.2 to 3%, e.g. about 0.5 to 2%; the proportion of anionic polymer is in the range of about 0.05 to 1%, e.g. in the range of about 0.1 to 0.5%, the proportion of the particular anionic polymer being generally insufficient in itself to form a gel such as that conventionally formed by the gum or other gelling agent in a toothpaste. in using toothpastes the amount of saliva generated in the mouth is often such as to cause considerable dilution, e.g. a fourfold dilution of the toothpaste. Accordingly it is desirable (when a foaming type of toothpaste is formulated) that the proportions of the active ingredients (cationic germicide and anionic polymer) in the toothpaste be greater than those in a mouthrinse (where the dilution in use may be only about 1:1 ½ vs. about 1:4 for instance); thus in one embodiment of this invention the concentrations of these ingredients in toothpaste are about 3 times given above for mouthrinses.

The serial dilution test, using tripticase soy broth is described in "Diagnostic Bacteriology", Fifth Edition, by Schaub, Foley, Scott and Bailey pub. 1958 by C.V. Mosby Co. Chapter 10 ("Test tube serial dilution method for determining susceptibility to antibiotics").

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. Process for treating teeth in the mouth which comprises providing at the surface of the teeth a sorbed complex of a cationic germicide and a water-soluble synthetic anionic polymer by applying to said surfaces under non-drying conditions an aqueous dispersion of said complex, the total concentration, in said dispersion, of said cationic germicide and said anionic polymer complexed therewith being less than about 0.5%, said complex being substantive to hydroxyapatite when hydroxyapatite is contacted with said dispersion, the concentration of each of said anionic polymer and said cationic germicide in said dispersion being at least about 0.01%.

2. Process as in claim 1 in which the cation:anion ratio is up to about 1:1.

3. Process as in claim 1 in which the anionic polymer has carboxyl groups and the number thereof in said combination is in excess of the number of cations of said germicide.

4. Process as in claim 1 which the total concentration of said cationic germicide and said anionic polymer complexed therewith is less than about 0.5%.

5. Process as in claim 4 in which the concentration of said germicide is below about 0.2%.

6. Process as in claim 1 in which said dispersion is a cloudy dispersion in which the average particle size is below 1 micron.

7. Process as in claim 6, in which said average particle size is below 0.7 micron.

8. Process as in claim 1 in which sai cationic germicide is a benzethonium salt.

9. Process as in claim 7 in which said anionic polymer has a molecular weight above 1000.

10. Process as in claim 1 in which said anionic polymer has a plurality of carboxyl groups.

11. Process as in claim 1 in which said anionic polymer is a copolymer of maleic acid and a vinyl lower alkyl ether.

12. Process as in claim 1 in which said anionic polymer is a copolymer of maleic acid and vinyl methyl ether.

13. Process as in claim 12 in which the molecular weight of said copolymer is up to about 1,000,000.

14. Process as in claim 1 in which there is applied to the teeth in the mouth an aqueous liquid containing said germicide and said polymer.

15. Process as in claim 1 in which said liquid is applied while said teeth are wet with saliva.

16. A process as in claim 7 in which said germicide is benzethonium chloride, said anionic polymer is a copolymer of one mol of methyl vinyl ether and one mol of maleic acid, and there is about 2/3 mol of said germicide per mol of maleic acid in the copolymer, the concentration of germicide in the dispersion being about 0.1%.

17. Process as in claim 7 in which said anionic polymer comprises a copolymer of maleic acid and said cationic germicide has a phenol coefficient of at least about 200.

18. Process as in claim 17 in which said anionic polymer is a copolymer of methyl vinyl ether and maleic acid and said germicide is a benzethonium salt.

19. An aqueous oral composition comprising a dispersed complex of a cationic germicide and a water-soluble synthetic anionic polymer, said cationic germicide being substantive to hydroxyapatite when hydroxyapatite is contacted with said composition, the total concentration, in said dispersion, of said cationic germicide and said anionic polymer complexed therewith being less than about 0.5%, and the concentration of each of said anionic polymer and said cationic germicide in said dispersion being at least about 0.1%.

20. An oral composition as in claim 19 containing added flavoring agent.

21. An oral composition as in claim 19 in which said anionic polymer comprises a copolymer of maleic acid.

22. A composition as in claim 21 in which said copolymer is a copolymer of one mol of methyl vinyl ether and one mol of maleic acid.

23. A composition as in claim 19 in which said cationic germicide has a phenol coefficient of at least about 200.

24. A composition as in claim 19 in which said cationic germicide comprises benzethonium chloride.

25. An aqueous oral composition comprising a dispersion of a complex of a cationic germicide and an anionic polymer prepared by mixing an aqueous solution of a soluble salt of said germicide and an aqueous solution of said polymer in such proportions that the number of cationic units is less than the number of anionic groups of said polymer.

26. A composition as in claim 25 in which the concentration of said complex is in the range of about 0.05 to 0.3% and the pH is in the range of about 4 to 9.

27. A composition as in claim 26 in which the particle size of the complex is below 1 micron.

28. A composition as in claim 25 containing added flavoring agent.

29. A composition as in claim 17 in which said germicide is benzethonium chloride, said anionic polymer is a copolymer of one mol of methyl vinyl ether and one mol of maleic acid, and there is about 2/3 mol of said germicide per mol of maleic acid in the copolymer, the concentration of germicide in the dispersion being about 0.1%.

30. An oral composition as in claim 27 in which said anionic polymer comprises a copolymer of maleic acid and said cationic germicide has a phenol coefficient of at least about 200.

31. An oral composition as in claim 30 in which said anionic polymer comprises a copolymer of maleic acid and said cationic germicide is a benzethonium salt.

* * * * *

UNITED STATES PATENT AND TRADEMARK OFFICE
CERTIFICATE OF CORRECTION

PATENT NO. : 3,956,480

DATED : May 11, 1976

INVENTOR(S) : Dichter et al

It is certified that error appears in the above—identified patent and that said Letters Patent is hereby corrected as shown below:

In column 20 line 26
(Claim 19 last line)  substitute

--0.01%--  for "0.1%"

Signed and Sealed this

Eighth Day of May, 1990

Attest:

HARRY F. MANBECK, JR.

Attesting Officer

Commissioner of Patents and Trademarks